United States Patent [19]

Gross

[11] Patent Number: 5,380,272
[45] Date of Patent: Jan. 10, 1995

[54] TRANSCUTANEOUS DRUG DELIVERY APPLICATOR

[75] Inventor: Joseph Gross, Moshav Mazor, Israel

[73] Assignee: Scientific Innovations Ltd., Yavne, Israel

[21] Appl. No.: 77,146

[22] Filed: Jun. 16, 1993

Related U.S. Application Data

[63] Continuation-in-part of Ser. No. 38,362, Mar. 29, 1993, abandoned, which is a continuation-in-part of Ser. No. 10,178, Jan. 28, 1993, abandoned.

[51] Int. Cl.$^6$ .............................................. A61N 1/30
[52] U.S. Cl. ..................................................... 604/20
[58] Field of Search ................... 604/20; 128/798, 802, 128/803, 639, 644

[56] References Cited

U.S. PATENT DOCUMENTS

| | | | |
|---|---|---|---|
| 4,708,716 | 11/1987 | Sibalis | 604/20 |
| 4,731,926 | 3/1988 | Sibalis | 604/20 |
| 4,865,582 | 9/1989 | Sibalis | 604/20 |
| 4,883,457 | 11/1989 | Sibalis | 604/20 |
| 5,002,527 | 3/1991 | Reller | 604/20 |
| 5,053,001 | 10/1991 | Reller et al. | 604/20 |

*Primary Examiner*—Gene Mancene
*Assistant Examiner*—Thomas Price
*Attorney, Agent, or Firm*—Mark M. Friedman

[57] ABSTRACT

A transcutaneous iontophoretic drug applicator, which includes an array of reservoirs which are electrically insulated from one another, some of which contain the drug to be administered. The applicator further includes a partially electrically conducting layer, preferably formed of two portions, each segments corresponding to an electrode, which overlies and contacts the reservoirs, and electrodes which overly and contact the partially electrically conducting layer. An electrical power source supplies power to the electrodes and causes the drug to be pushed out of the reservoirs and into the skin. The applicator is designed to keep the local current flux below threshold irritation and burn levels regardless of variations in electrical skin resistance.

17 Claims, 8 Drawing Sheets

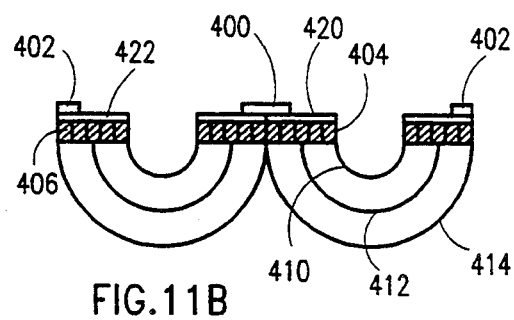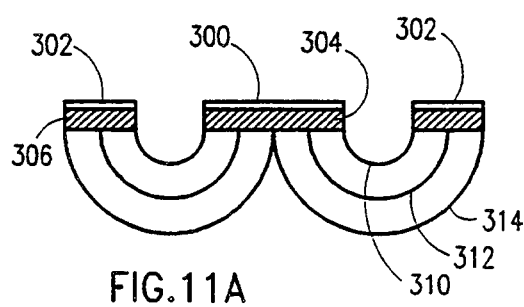
FIG.11B  FIG.11A
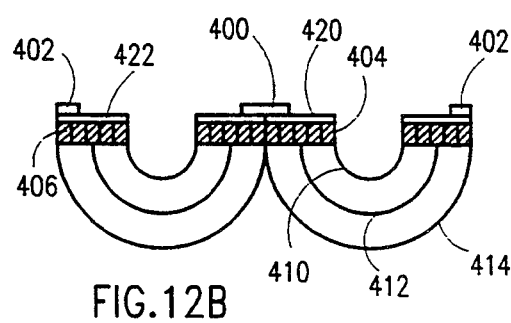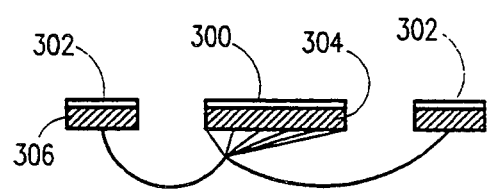
FIG.12B  FIG.12A
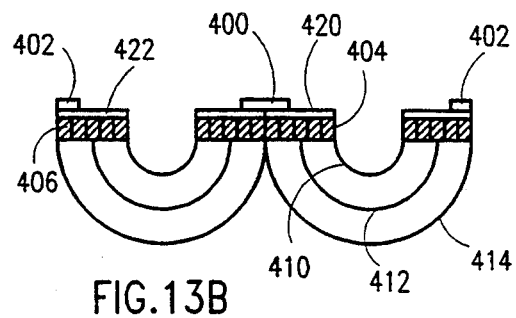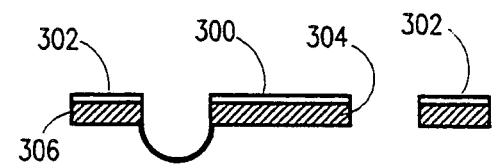
FIG.13B  FIG.13A

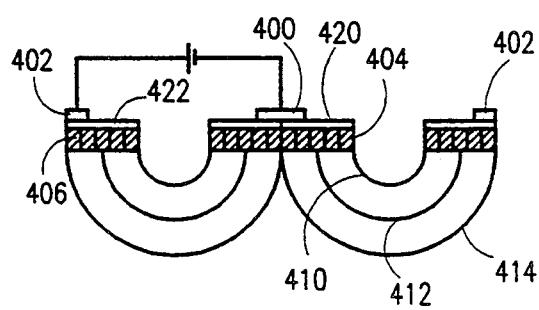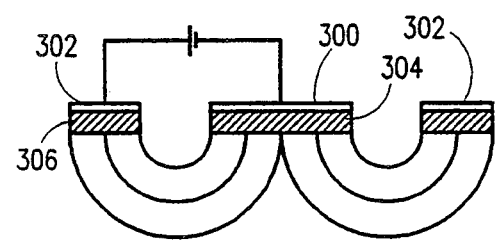
FIG.14B  FIG.14A
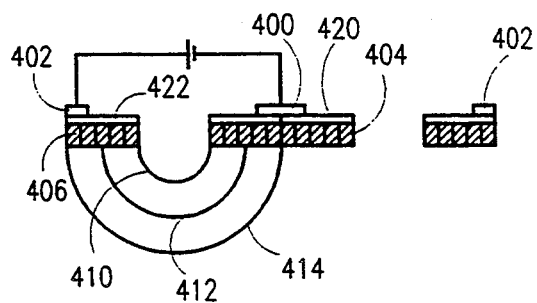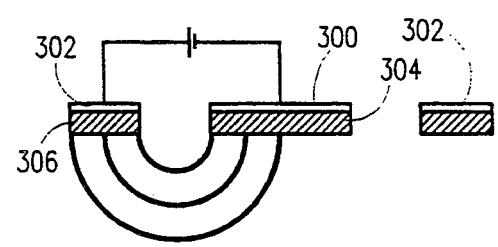
FIG.15B  FIG.15A

TRANSCUTANEOUS DRUG DELIVERY APPLICATOR

This is a continuation-in-part of U.S. patent application Ser. No. 08/038,362, filed Mar. 29, 1993, now abandoned which is a continuation-in-part of U.S. patent application Ser. No. 08/010,178, filed Jan. 28, 1993, now abandoned.

FIELD AND BACKGROUND OF THE INVENTION

The present invention relates to transcutaneous, or transdermal, drug delivery systems and, more particularly, to an applicator for use in the transcutaneous iontophoretic delivery of drugs.

A variety of methods for delivering various drugs to patients are in use. For example, many medications are taken orally. The drugs thus ingested are picked up by the blood system in the stomach and intestines and delivered throughout the body.

Another delivery method involves the introduction of the drug directly into the blood stream by injection into a vein of the patient. Such delivery may be made using a syringe for the essentially instantaneous delivery of the drug dosage or a more uniform and prolonged delivery may be achieved by using extended intravenous delivery.

A third delivery method, which is gaining increasingly wide acceptance, involves the transcutaneous transfer of drug, i.e., the transfer of drug into the patient across the skin. In certain circumstances, the transcutaneous delivery of drugs offers significant advantages over other delivery methods. Transcutaneous delivery is particularly advantageous in that it offers the possibility of the continuous and measured delivery of drugs to the body without the complications and inconveniences of intravenous delivery.

Such a measured delivery of drug over a relatively long period of time is particularly desirable in the delivery of drugs which could be harmful if administered in large dosages and for drugs, such as various types of pain relievers, which are most effective when delivered continuously.

A number of transcutaneous drug delivery systems are known. Perhaps the simplest involves placing the drug in contact with the skin and allowing the drug to penetrate the skin by osmosis and/or related spontaneously occurring mass transport phenomena. This technique is commonly used, for example, to administer nitroglycerine.

A more sophisticated transcutaneous drug delivery technique, known as iontophoresis, uses electrical energy to actively cause the drug to penetrate the skin and allows for better control of the rate of drug delivery and its depth of penetration.

Stripped to its bare essentials, iontophoresis involves the application of an electromotive force to drive ionic chemicals, typically drugs, through the skin so that they can be absorbed by the underlying tissues and nearby blood vessels.

An iontophoretic device includes two electrodes. One of the electrodes has in its vicinity the ionic species to be driven into the skin. The other electrode, in close proximity to the first electrode, serves to close the electrical circuit through the body. In use, both electrodes are brought in contact with the skin. An electromotive force is applied to the electrodes which creates an electrical circuit between the two electrodes which runs through the skin and underlying tissues and which drives the ionic drug species away from the first electrode and through the skin.

The iontophoretic transcutaneous delivery of drugs, as presently practiced, is not without its problems. Chief among these is the difficulty in ensuring a relatively uniform low electrical flux across the two electrodes.

It has been widely appreciated that the difficulty in maintaining appropriate electrical flux stems from the difficulty in creating and sustaining good contact between the device and the skin. The skin is normally a rough surface and even when the area onto which the electrodes are to be applied has been shaved of all hair, the remaining surface remains three-dimensional and contains various imperfections and inhomogeneities, such as cut hairs, follicles, cuts, scar tissue, and the like, which militate against the formation of good electrical contact between the applicator and the skin.

Various conducting gels, with and without various flux improving components, have been used to fill the space between the applicator and the skin in order to at least partially overcome some of the difficulties which arises when attempts are made to uniformly contact the essentially flat applicator and the microscopically highly three-dimensional surface of the skin.

Another way of ensuring better contact between the electrodes and the skin is described in U.S. Pat. No. 4,708,716 and involves the use of an applicator which features a plurality of electrodes which are flexibly connected to each other so that the entire applicator is better able to flex and conform itself so as to better echo the macro contours of the skin surface on which the applicator is deployed.

This solution, while useful on the macro scale in conforming the overall shape of the applicator to the shape of the skin surface, is ineffective in overcoming the difficulties caused by imperfections and inhomogeneities in the skin. Some of these features, for example cuts in the skin, present an electrical path which offers significantly lower electrical resistance than the surrounding skin. The lowered resistance brings about the concentration of current in and around the imperfection and, if the local current flux rises sufficiently, can bring about undesirable consequences such as tingling, irritation and even burns. The phenomenon is further aggravated by the fact that the initial concentration of current causes a further decrease in the local resistance and a further increase in the local current. This snowball effects serves to quickly create a 'hot spot' which suffers irritation and burns.

Various methods and procedures have been developed or suggested to limit or eliminate such galvanic burns. The general objective is to keep the localized current density, that is, the current per unit area of skin, to below the threshold values at which burns, or unacceptable irritation, can be encountered.

Current density uniformity can be enhanced by avoiding folds, wrinkles and other avoidable inhomogeneities between the applicator and the skin and by using various gel-moistened pads between the electrode and the skin. However, such techniques are ineffective in avoiding irritation and burns caused by the concentration of electrical current as a result of unavoidable, and often undetected, imperfections in the skin, such as microscopic cuts or punctures.

One possible solution is to use an array of electrodes, each of which is connected in parallel to a power source through a dedicated resistor. Each resistor is of a resistance which is relatively large compared to the resistance normally encountered in penetrating the skin. In this way, changes in skin surface resistance cause little effect on the current density.

Transcutaneous drug delivery systems typically employ a current flux of as low as 0.0001 ampere per square centimeter of skin surface, while the electrical resistance of the skin to current flow is on the order of 6 to 9K ohms.

Thus, if a typical power source, such as a 1.5 volt battery, is to be used, the total system resistance per square centimeter of skin surface should be approximately 15 K ohms. Part of this resistance is attributable to the battery resistance and the resistance of various other components of the applicator through which the current travels. The balance of the resistance, which is typically the bulk of the total resistance, is contributed by a dedicated current limiting device, typically a resistor, which is included in the electrical circuit in series with each electrode.

When the skin resistance of a particular location on the skin is significantly lower, as when an open cut is encountered, the local skin resistance drops significantly. However, since the skin resistance constitutes only a small fraction of the local overall resistance, the local overall current increases only slightly and remains below the values which would cause irritation or burns.

The difficulty with such a configuration is that the device described therein is very difficult to build, and thus costly. A related disadvantage is that such a device, being made up of a large number of individual electrodes and resistors, could be unreliable and suffer from an unacceptably short storage and operational life.

There is thus a widely recognized need for, and it would be highly desirable to have, a iontophoretic transcutaneous drug applicator which would have the property of effectively limiting the current flux introduced to the skin to safe levels and which would, at the same time, be very inexpensive to manufacture and highly durable and rugged during storage and use.

SUMMARY OF THE INVENTION

According to the present invention there is provided a transcutaneous iontophoretic chemical applicator, comprising: (a) an array of reservoirs, the reservoirs being electrically insulated from one another, at least one of the reservoirs containing the chemical; (b) a partially electrically conducting layer overlying and contacting at least two of the reservoirs; (c) electrodes contacting and at least partially overlying the partially electrically conducting layer such that different portions of current flowing between the electrodes travel through different distances through the partially conducting layer so as to tend to equalize the overall path resistance of the different portions of current; and (d) an electrical power source electrically connected to the electrodes.

According to further features in preferred embodiments of the invention described below, the electrodes include a single pair of electrodes.

According to still further features in the described preferred embodiments the partially electrically conducting layer, which may be made of a semiconductor, is made up of a single layer overlying all of the reservoirs.

According to yet further features in the described preferred embodiments, the partially electrically conducting layer, is made up of two layers, each overlying substantially one half of the reservoirs.

The present invention successfully addresses the shortcomings of the presently known configurations, by providing, in a preferred embodiment, a transcutaneous drug applicator which is made up of an array of reservoirs, some of which contain the drug to be delivered, which reservoirs are overlayed by a single layer, or by a pair of adjoining layers, made of a material which is partially conducting and which serves to significantly increase the electrical resistance of the circuits through each of the reservoirs. The partially conducting layer or layers is or are, in turn, overlayed with one of the two electrodes which serve to evenly distribute the current across the reservoirs.

BRIEF DESCRIPTION OF THE DRAWINGS

The invention is herein described, by way of example only, with reference to the accompanying drawings, wherein:

FIG. 11A shows a conventional circular applicator;

FIG. 11B shows a circular applicator according to the present invention;

FIG. 12A shows how the current lines of an applicator as in FIG. 11A concentrate at the site of an inhomogeneity;

FIG. 12B shows that current lines of an applicator as in FIG. 11B remain largely unchanged;

FIG. 13A shows how the current lines of an applicator as in FIG. 11A concentrate at the site of a short circuit;

FIG. 13B shows that current lines of an applicator as in FIG. 11B remain largely unaffected by a short circuit;

FIG. 14A shows that the voltage drop across an applicator as in FIG. 11A is constant when the applicator is properly placed;

FIG. 14B shows that the voltage drop across an application as in FIG. 11B is constant when the applicator is properly placed;

FIG. 15A shows that the voltage drop across an application as in FIG. 11A is the same regardless of whether the applicator is properly or improperly placed;

FIG. 15B shows that the voltage drop across an application as in FIG. 11B is very different when the applicator is improperly placed than it is when the applicator is improperly placed.

DESCRIPTION OF THE PREFERRED EMBODIMENTS

The present invention is of an inexpensive yet rugged transcutaneous drug delivery applicator which has the ability of effectively limiting the amount of current which is able to reach specific locations on the skin.

The principles and operation of an applicator according to the present invention may be better understood with reference to the drawings and the accompanying description.

Figure 1:
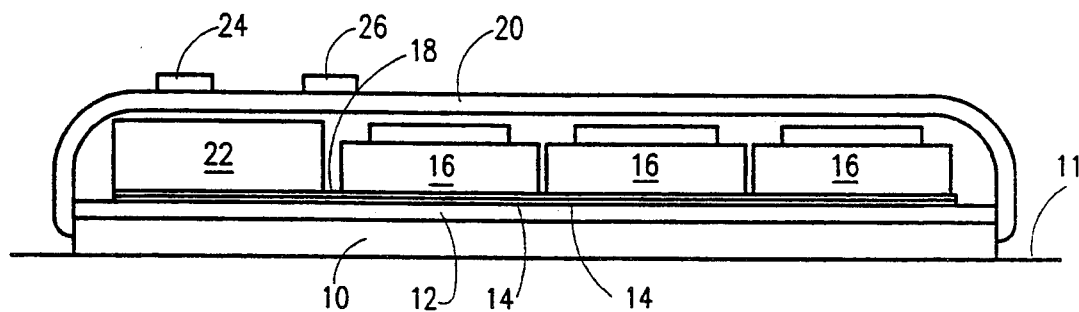
FIG. 1 is a side cross-sectional view of an applicator according to the present invention.
Figure 1A:
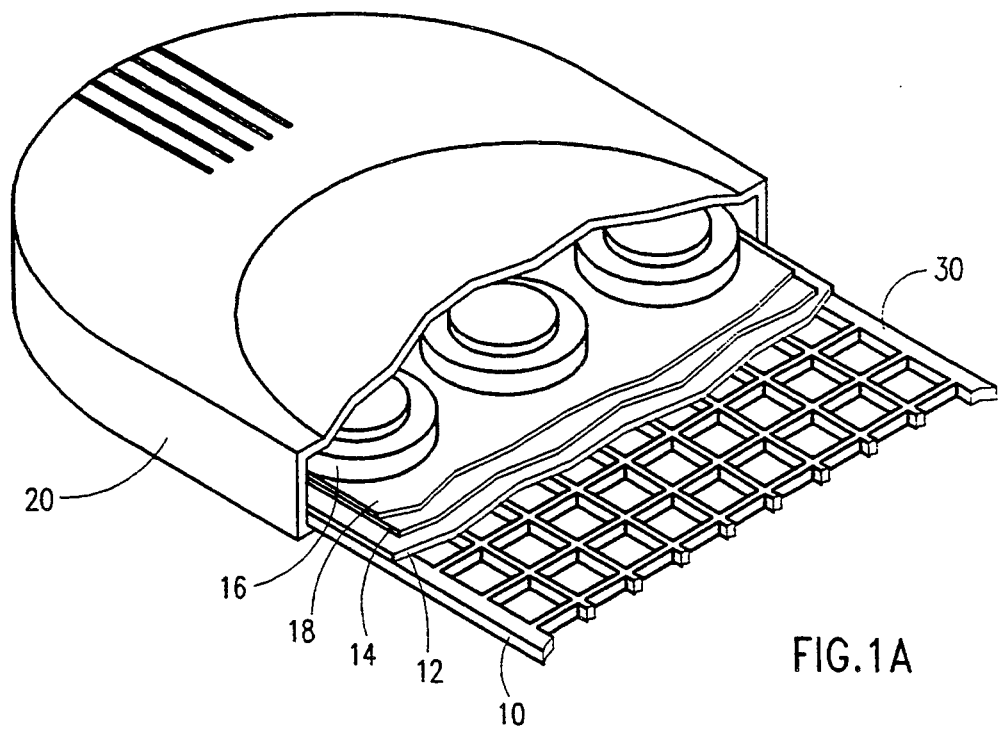
FIG. 1A is a perspective cross-sectional view of an applicator according to the present invention.

Referring now to the drawing, FIGS. 1 and 1A illustrate, in cross-section, one embodiment of an applicator according to the present invention. The illustrated applicator is made up of a number of components which will be identified next and whose structure and function will be described in more detail below.

Specifically, the applicator includes a reservoir array 10 at its side nearest the skin 11 onto which the device is to be applied. Located immediately above, and in contact with, reservoir array 10 is a partially electrically conducting layer 12 which may be made of a single layer or which alternatively be made of two adjoining layers lying side by side, as is described below. While partially electrically conducting layer 12 will be referred to in the singular throughout the specification and in the claims, it is intended that such terminology also includes the case where the layer is made up of two or more segments which lie in substantially the same plane and which approximately adjoin each other but are preferably somewhat separated from each other. Located immediately above, and in contact with, partially electrically conducting layer 12 is a pair of electrodes 14. Above electrodes 14 lie an array of batteries 16, or other suitable power source, as described below, which are electrically connected to each other and to electrodes 14 is some suitable manner which will be described below. Batteries 16 may be electrically insulated from electrodes 14 by an insulating layer 18 interposed between electrodes 14 and batteries 16. Batteries 16 and the entire assembly is enclosed in a suitable casing or housing 20 which may also enclose an activator or microprocessor 22 for controlling the operation of the applicator and may further feature an activation button 24 and a bolus button 26, as will be described below.

Each of the above-identified components will next be further described with reference to FIG. 1 and further in reference to FIGS. 2-6 which form a series of perspective construction diagrams showing the shape and location of the various key components of an applicator according to the present invention.

Shown in FIG. 1 is a view of reservoir array 10 which forms the lowest components of an applicator according to the present invention, i.e., the component which comes in direct contact with skin 11 of the patient, and which contains the drug to be administered to the patient.

Reservoir array 10 may be of any suitable length, width and height and may be made of any suitable material, preferably silicon, provided that the reservoirs are electrically insulated from each other. Preferably, as shown in FIG. 2, reservoir array 10 is made of a single electrically insulating body which is formed with an array of preferably regularly shaped volumes 30 integrally formed therein.

Figure 2:
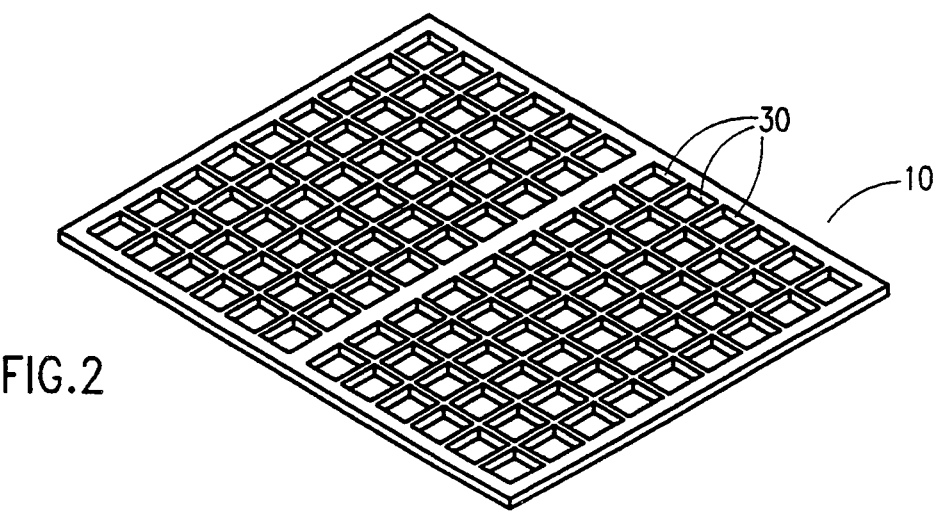
FIG. 2 is a perspective view of a reservoir array.

The square honeycomb structure shown in FIG. 2 is illustrative only. It will be appreciated that many other shapes of volumes 30 are possible, including but not limited, rectangular, hexagonal or circular, and the like. It will also be appreciated that the dimensions of each of volumes 30 as well as the overall dimensions of reservoir array 10 may be varied as required to meet specific needs. It will similarly be appreciated that volumes 30 may alternatively be irregular microscopic, or smaller, structures, such as the pore structure of a suitable insulating material.

The volume 30 are filled with suitable electrically conductive material, such as various electrically conductive gels. Some of volumes 30 contain, in addition, suitable amounts of one or more drugs, typically suspended or dissolved in the conductive gel. In the example of FIG. 2, it will be assumed for purposes of illustration that half of volumes 30, say, the 54 reservoirs nearest the viewer, contain drug, while the other 54 do not.

The drugs included in some of volumes 30 are either in ionized form or become ionized upon the application of an electric field. The charge of the ionized drugs is the same as that of volumes 30 wherein it is located, which causes the drug to be driven out of its volumes 30 and into skin 11 which immediately underlies it.

The electrically conductive gel is typically sufficiently viscous as to remain in volumes 30 while the drug molecules make their way, under the influence of the electromotive force, through the gel and into the skin. Prior to use, the bottom portion of the reservoir array 10 may be covered with a disposable sealing layer (not shown) which is removed just prior to the deployment of the applicator. Alternatively or additionally, the bottom-directed openings of volumes 30 may be covered by a microporous or semi-permeable membrane which allows drug molecules to leave volume 30 but which prevents the escape of the conductive gel.

Figure 4:
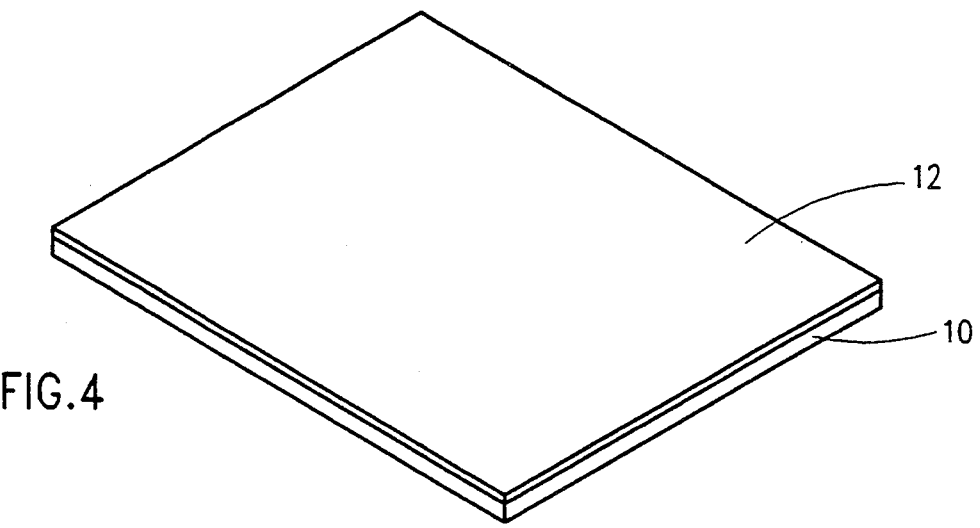
FIG. 4 is a perspective view of the reservoir array and partially electrically conducting layer of FIG. 3 as they appear when joined together.
Figure 4A:
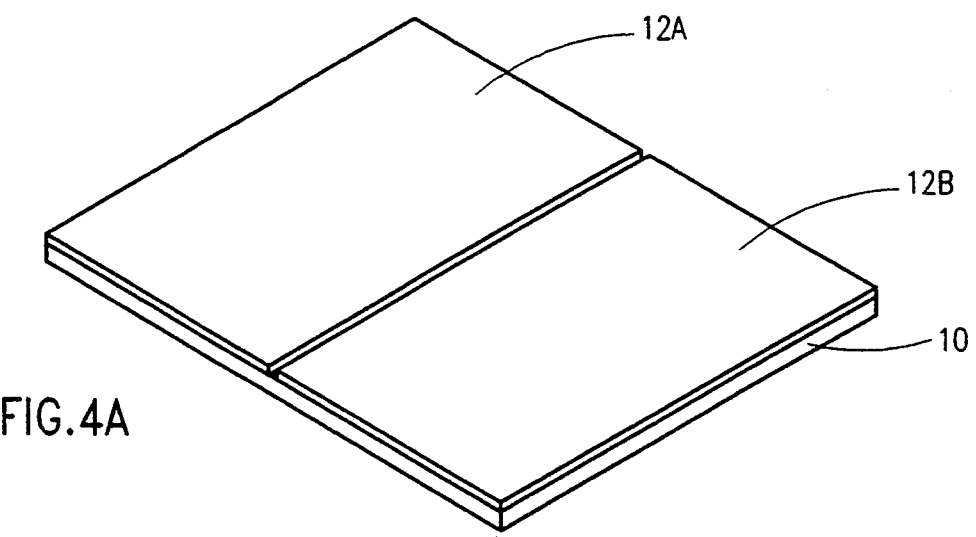
FIG. 4A is a perspective view of the reservoir array and partially electrically conducting layer of FIG. 3 as they appear when joined together, where the partially electrically conducting layer is made of two adjoining portions.
Figure 3:
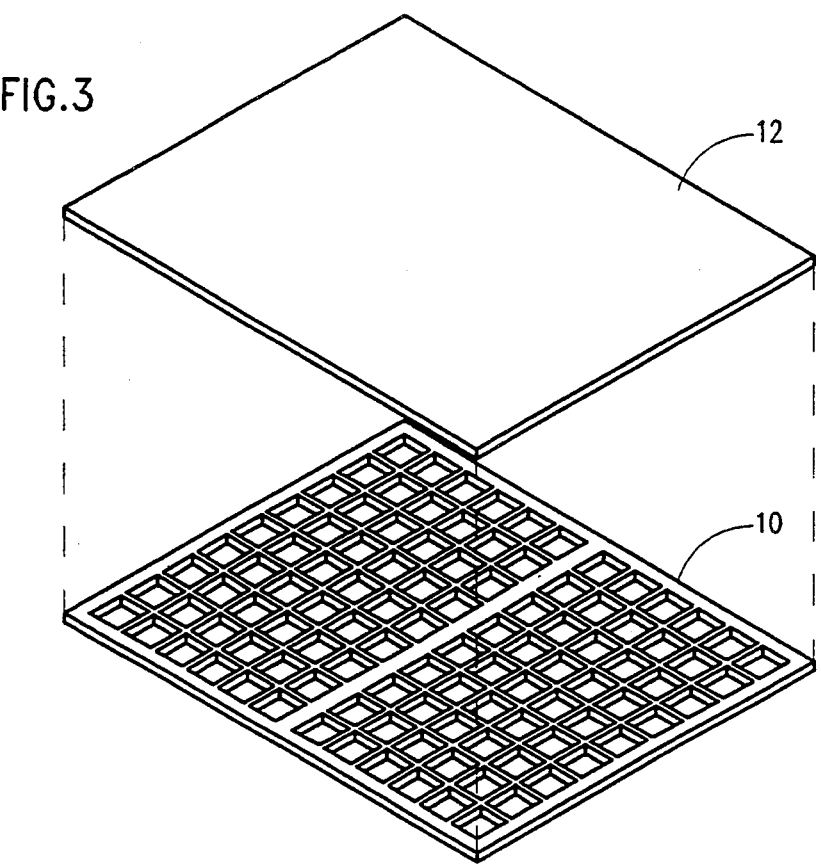
FIG. 3 is a perspective exploded view of a reservoir array and a partially electrically conducting layer made of a single integral layer.
Figure 3A:
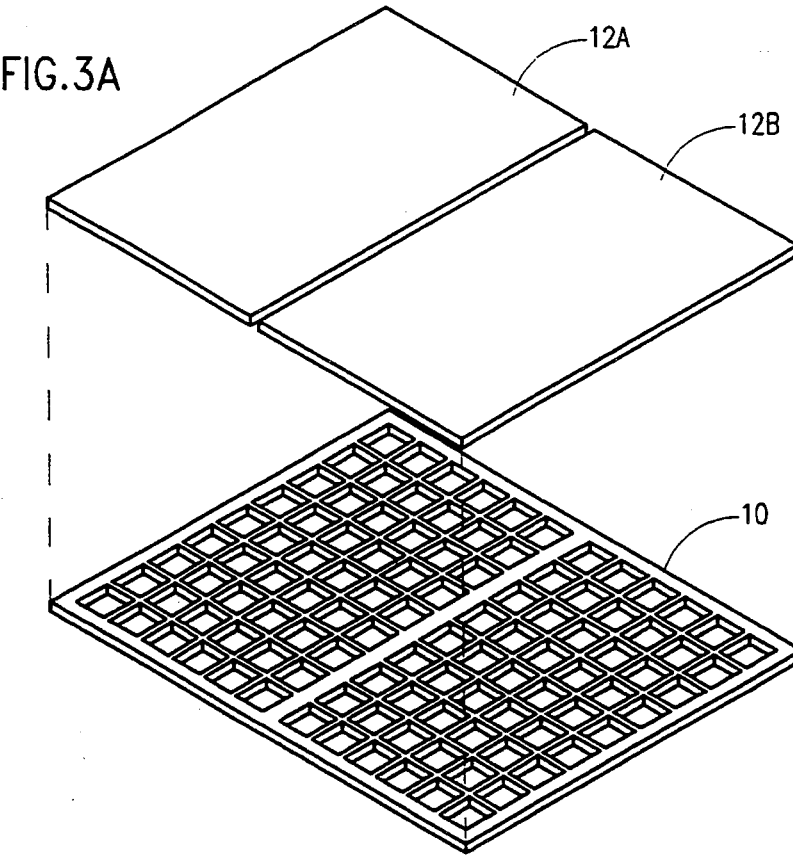
FIG. 3A is a perspective exploded view of a reservoir array and a partially electrically conducting layer made of two adjoining portions.

As can best be seen in FIGS. 3 and 4, overlying at least two volumes 30 of reservoir array 10, and, preferably, laminated, deposited or painted onto it, or co-injected with it, is partially electrically conducting layer 12. In one embodiment, shown in FIG. 3, a single partially electrically conducting layer 12 overlies all volumes 30 of reservoir 10. In a preferred embodiment shown in FIGS. 3A and 4A, partially electrically conducting layer 12 is made up of two segments, 12a and 12b, somewhat separated from each other, each of which overlies a portion, preferably substantially one half, of volumes 30 and which preferably substantially correspond in extent and coverage with the two electrodes described below. Splitting partially electrically conducting layer 12 into two segments aids in further electrically separating the zones of influence of the two electrodes. Partially electrically conducting layer 12, or 12a and 12b, may be made of any suitable material, such as electrically conducting polymers such as suitable vinyls or epoxies or carbon loaded or surface metallized plastics. Preferably, partially electrically conducting layer 12, or 12a and 12b, is made up of a semiconducting material, such as silicon containing carbon (graphite) particles.

The nature and thickness of partially electrically conducting layer 12 are such that current is able to flow through it in the perpendicular direction, where the layer is relatively thin, but that essentially no current is able to flow transversely through the layer because of the great thicknesses involved. Thus, partially electrically conducting layer 12 presents a certain suitably selected resistance to current flow in the direction perpendicular to its large surfaces but offers virtually infinite resistance to current flow in the direction parallel to its large surfaces, thereby causing current to flow directly downward through the layer and virtually preventing any current from flowing sideways. Partially electrically conducting layer 12 thus in effect constitutes an array of resistors of suitable resistive value in the vertical direction but without the large expense and operational difficulties of dedicated discrete resistors and electrodes for each of the reservoirs.

Figure 5:
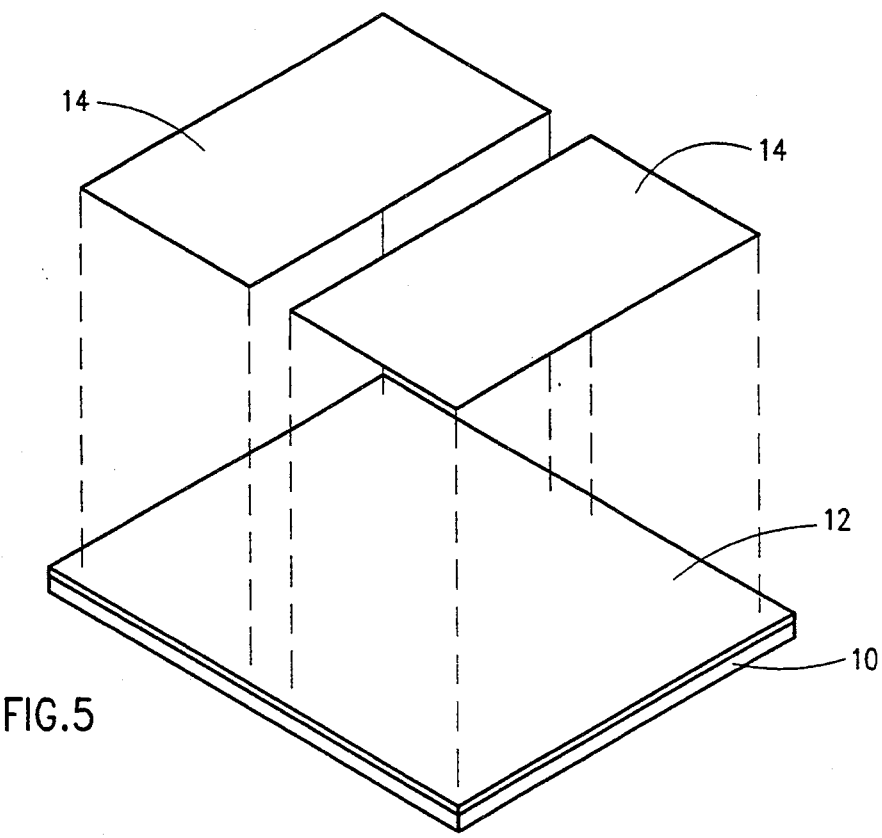
FIG. 5 is a perspective exploded view of a reservoir array joined with a partially electrically conducting layer and a pair of electrodes.
Figure 5A:
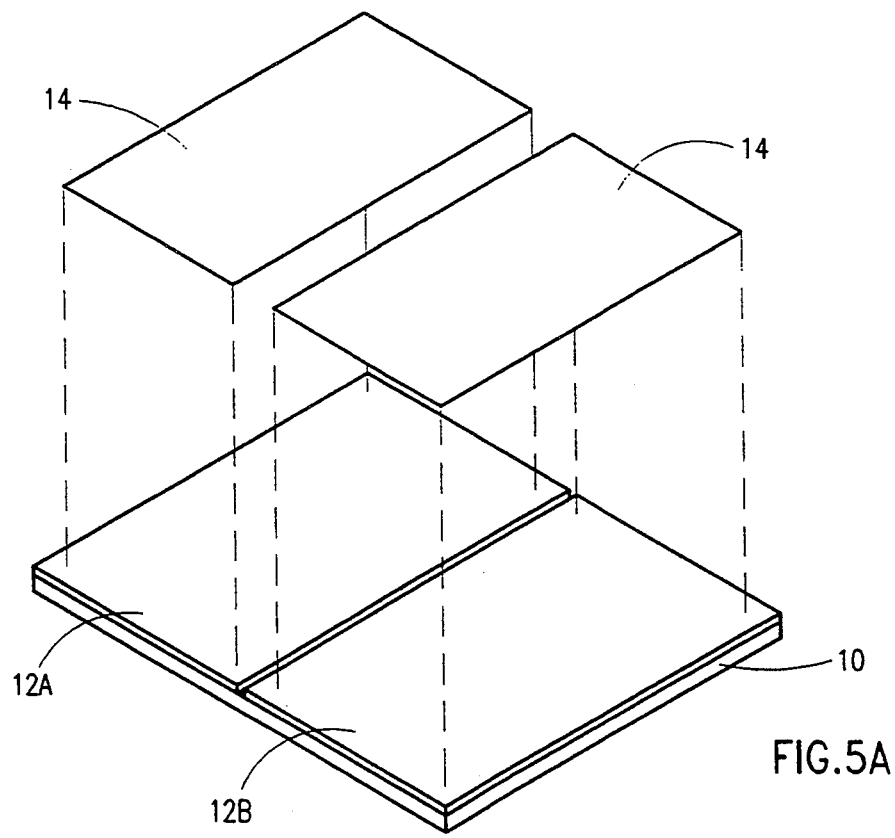
FIG. 5A is a perspective exploded view of a reservoir array joined with a partially electrically conducting layer and a pair of electrodes, where the partially electrically conducting layer is made of two adjoining portions.
Figure 6:
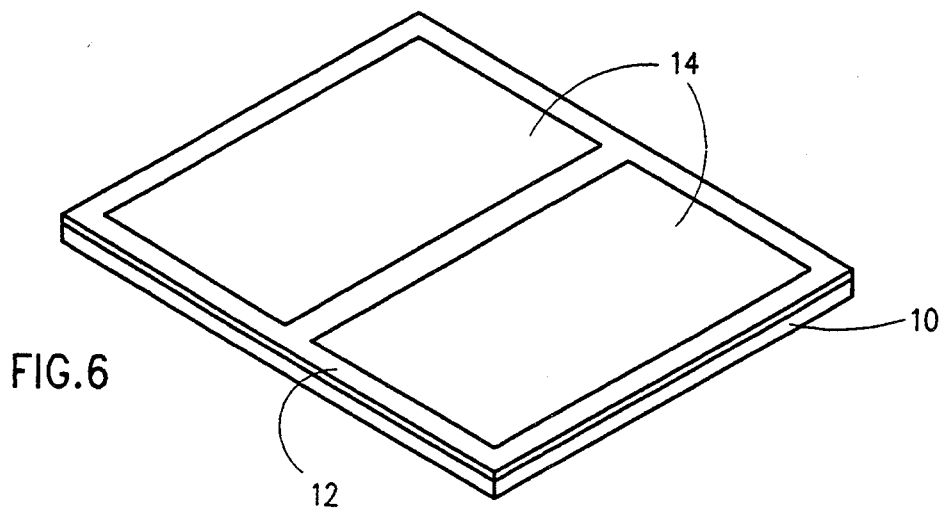
FIG. 6 is a perspective view of the reservoir array, partially electrically conducting layer and electrodes of FIG. 5 as they appear when joined together.
Figure 6A:
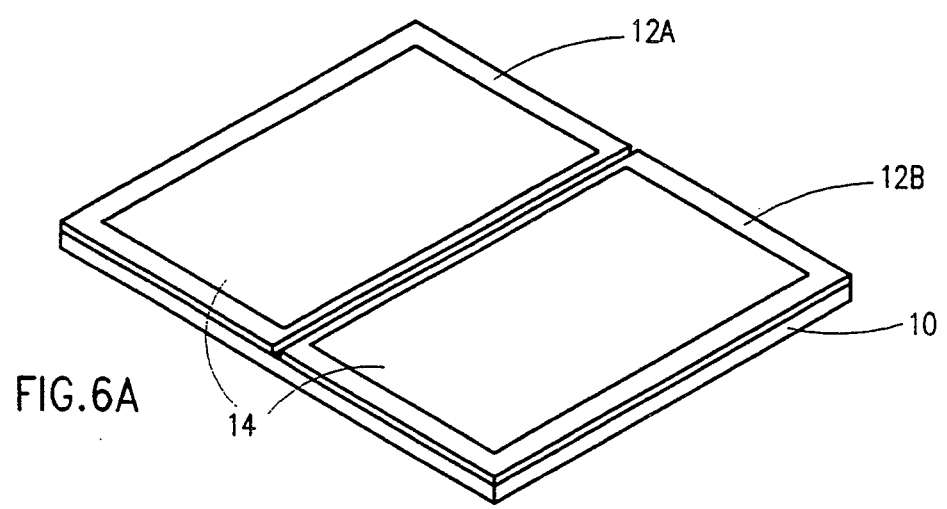
FIG. 6A is a perspective view of the reservoir array, partially electrically conducting layer and electrodes of FIG. 5 as they appear when joined together, where the partially electrically conducting layer is made of two adjoining portions.

As can best be seen in FIGS. 5 and 6 and FIGS. 5A and 6A, overlying partially electrically conducting layer 12, or 12a and 12b, and preferably laminated onto it, are electrodes 14 which may be made of any suitable material including, but not limited to, aluminum or other metallic foil or conductive rubber or resin film. Shown in FIGS. 5 and 6 and in FIGS. 5A and 6A is a preferred embodiment wherein a single pair of electrodes 14 is used, each electrode covering approximately half of the active surface of the applicator, corresponding to approximately half of the reservoirs. In the configuration of FIGS. 5A and 6A the two portions of partially electrically conductive layer, 12a and 12b, substantially correspond in their coverage to that of electrodes 14. It will, however, be readily appreciated that it is possible to use an array of pairs of electrodes, for example with each member of each pair of electrodes overlying one or a small number of volumes 30.

Figure 7:
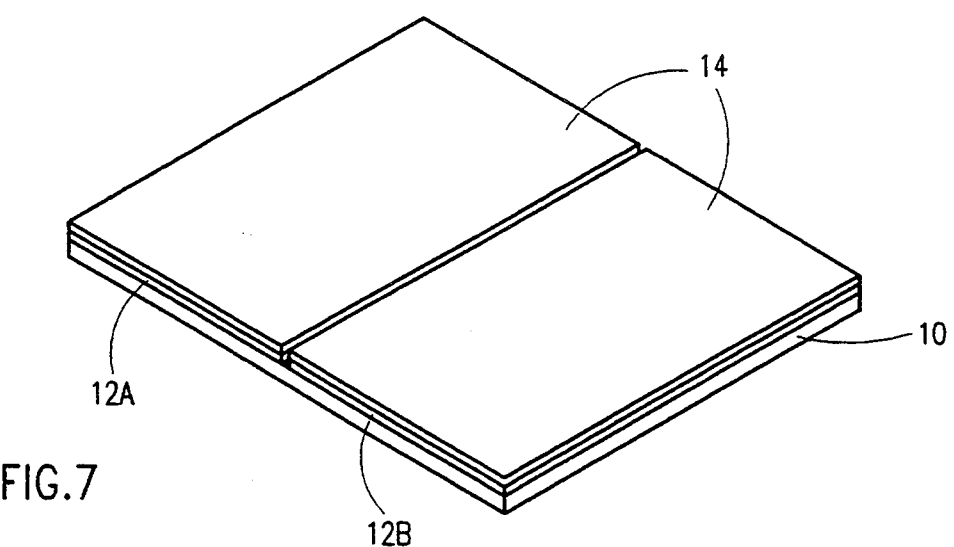
FIG. 7 is a perspective view of the reservoir array, a two-portion partially electrically conducting layer as in FIG. 6A wherein the electrodes cover the entire upper surface of the partially electrically conducting layer.

Shown in FIG. 7 is another embodiment wherein electrodes 14 extend to fully cover the entire surface of partially electrically conducting layer 12, or 12a and 12b. Such a configuration makes it easier to laminated or co-inject electrodes 14, preferably made of a suitable plastic impregnated with conductive components, such as graphite, to form a monolithic structure.

Figure 8:
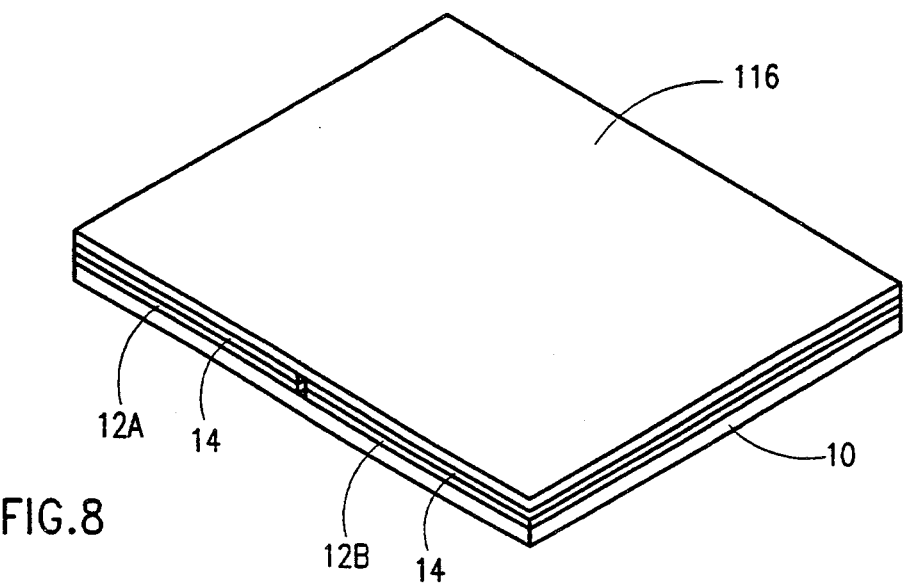
FIG. 8 is a perspective view of the reservoir array, a two-portion partially electrically conducting layer, a pair of electrodes and an energy source in the form of a flat layer.

A device according to the present invention further includes a suitable electrical power source, preferably batteries 16 (FIGS. 1 and 1A), which is electrically connected in some suitable fashion (not shown) to electrodes 14. Preferably, the power source is an array of miniaturized batteries, for example, those used in electrically driven watches, which are connected in series. It will be appreciated that a variety of power sources, including any of a large number of possible batteries configured in any suitable manner, may be employed. For example, the power source may be in the form of a energy providing layer 116 located directly above electrodes 14, as shown in FIG. 8. Energy providing layer 116 may be made of a suitable plastic material and may be laminated onto, or be co-injected with, the layer or layers which it overlies.

Figure 9:
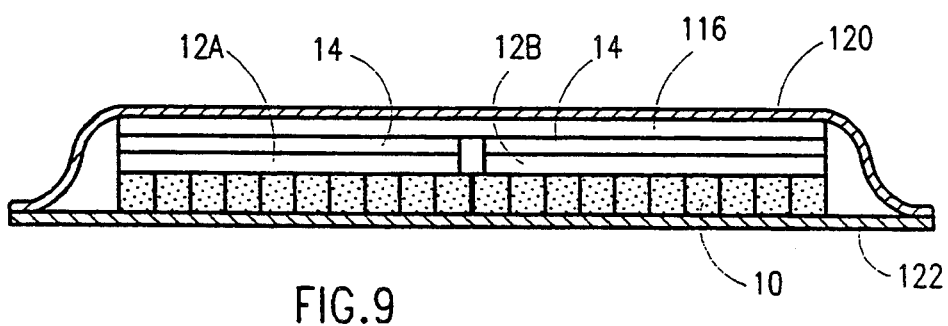
FIG. 9 is a side cross sectional view of an embodiment of an applicator according to the present invention having a removable seal.

Preferably, an applicator according to the present invention, especially one as described in connected with the embodiment of FIG. 8, comes in pre-packaged, disposable units which are ready for application to the skin. Preferably, as shown in FIG. 9, each applicator comes packaged in a housing which is made up of two portions—an upper casing 120 which is preferably permanently attached to the applicator, or may be an integral part thereof, and a removable seal 122 which seals reservoir array 10 prior to deployment of the applicator.

Figure 10:
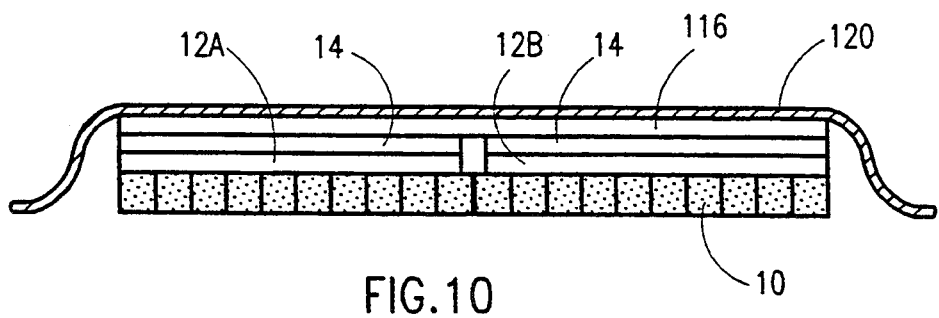
FIG. 10 is a view of the applicator of FIG. 9 following the removal of the removable seal.

Prior to use, upper casing 120 and removable seal 122 are connected to each other around their adjoining peripheries. Any suitable means can be used to effect this connection. Just prior to use, removable seal 122 is stripped off and discarded exposing the lower portions of reservoir array 10 (FIG. 10) and the periphery of upper casing 120. The newly exposed surfaces of upper casing 120 feature a suitable adhesive material which will aid in retaining the applicator on the skin after the applicator has been pressed onto the skin. Preferably, the lowermost surfaces of solid elements making up reservoir array 10, e.g., the insulator walls, also feature a suitable adhesive. The presence of adhesive at these points makes for a more uniform contact between reservoir array 10 and the skin of the user.

The electrical connection between the power source and electrodes 14 may be effected by various means, including, but not limited to, the use of electric lead wires, metal foil, and the like.

The top portion of an applicator according to the present invention may be sealed by any convenient casing or housing 20, including, but not limited to a plastic cover or backing. Casing or housing 20 may, in preferred embodiments according to the present invention, also include an activator or similar means for turning the power supply on and off. In this regard, casing or housing 20 may feature an activation button 24.

Casing or housing 20 may further include a bolus button 26, which will allow for the temporary increase the rate of drug injection. Such increases are often desirable in the administration of pain killers where the patient desires to temporarily increase the dosage to meet unusually strong pains. It is to be noted that because an applicator according to the present invention is designed to limit the local current density applied to the skin, a bolus delivery mechanism may be readily use without fear of irritation or burns.

Preferably, an applicator according to the present invention further includes a microprocessor 22 for controlling the rate of administration of the drug. Microprocessor 22 may be used to administer the drug based on one or more of several pre-determined program which may be fixed by the drug manufacturer, the physician and/or the patient to optimize the drug delivery by maximizing the effectiveness of the drug and minimizing any deleterious effects.

While the embodiments described heretofore are based, for illustrative purposes, on a reservoir array which is made up of two adjoining essentially square or rectangular matrices of medicine-containing sets of volumes, it will be readily appreciated that many other geometries are possible.

For example, a device according to the present invention could be configured with one of the sets of volumes located centrally and surrounded by a second set of volumes which forms an annulus around the first set. That is, the applicator could, for example, be circular with one electrode (say, the anode) and its associated medicine-containing volumes located at or near the center of the circle while the second electrode (say, the cathode) and its associated medicine-containing volumes form a ring around the first electrode.

Shown in FIGS. 11-15 are cross-sectional views of such circular applicators as they would appear when applied to the skin of the patient (not shown), with FIGS. 11A, 12A, 13A, 14A and 15A showing prior art applicators while FIGS. 11B, 12B, 13B, 14B and 15B show corresponding applicators according to the present invention.

A conventional circular applicator (FIG. 11A) includes a central electrode 300 and an annular electrode 302, completely overlying, respectively, a central common reservoir 304 and an annular common reservoir 306. Also shown in FIG. 11A are the locations within the skin of the patient (not shown) of three representative electrical current lines 310, 312, and 314. It will be appreciated that current line 310, which is closest to the applicator and which is the shortest of the current lines shown, will pass more current that will current line 312 which is longer. Current line 312, in turn, will pass more current than current line 314 which is longer yet. The relative amount of current passed is indicated schematically by the thickness of the current lines.

The reason for the different current magnitudes is that current following the longer current lines must traverse more skin resistance than does current passing through the shorter paths. The consequences of such a current strength differential are highly undesirable, resulting in uneven distribution of the drug to the skin, with the shorter current lines carrying the bulk of the medicine while the longer lines carry little or no medicine. In addition, the concentration of the current could lead to hot spots and the attendant irritation or burns, as described in more detail below.

Shown in FIG. 11B is a circular applicator according to the present invention. Here a central electrode 400 and an annular electrode 402 partly overly, respectively, a central partially electrically conducting layer 420 and an annular partially electrically conducting layer 422, which may be made of materials similar to those described in the context of the basic embodiments of FIGS. 1-10. Central partially electrically conducting layer 420 and annular partially electrically conducting layer 422, in turn, overly, preferably completely, a central partitioned reservoir 404 and an annular partitioned reservoir 406.

As described in the context of the embodiments of FIGS. 1-10, current from the electrodes goes through the partially conducting material, into the individual volumes of the reservoirs and into the skin. The relative size and dimensions of electrodes 402 and 404 and of reservoirs 404 and 406 and their relative placement, as well as the properties and dimensions of partially conducting layers 420 and 422 are selected to reduce the disparity in the total resistance of the various current paths so that, substantially all the paths of current between central electrode 400 and annular electrode 402 tend to be of substantially equal total overall resistance and therefore carry substantially equal currents, as indicated by current lines 410, 412, and 414, which are indicated visually with lines of the same thickness.

It will be seen, for example in FIG. 11B, that current following current line 414 goes from annular electrode 402, directly through the thickness of annular partially electrically conducting layer 422, through one of the volumes of annular reservoir array 406, through the skin via current line 414, through one of the volumes of central reservoir array 404, directly through the thickness of central partially electrical conducting layer 420, and to central electrode 400.

By contrast, current following current line 410 leaves annular electrode 402 and must travel transversely across annular partially electrical conducting layer 422 from a position near its outer periphery to a position near its inner periphery while at the same time the current must go through the thickness of annular partially electrical conducting layer 422. The current must then go through one of the volumes of annular reservoir array 406, through the skin via current line 410, through one of the volumes of central reservoir array 404. The current must then traverse the thickness of central partially electrical conducting layer 420 while also traveling across it from a point near its outer periphery to a point near its center where central electrode 400 is located.

The well-designed additional travel through the partially conducting layers of all but the most penetrating current lines tends to equalize the overall resistance of each current path and therefore effects a uniform distribution of current across the applicator, reducing or eliminating the chance for hot spots and ensuring a uniform delivery of the medicine to the patient.

Some of the consequences and advantages of a configuration such as that shown in FIG. 11B are illustrated in FIGS. 12-15. Schematically depicted in FIG. 12A is the occurrence of a hot spot using a conventional applicator. When an inhomogeneity 330 is encountered, current lines tend to concentrate creating a hot spot which could produce irritation or even burns. By contrast, an applicator according to the present invention, as shown in FIG. 12B, creates a uniform zone of low current density. When an inhomogeneity is encountered only a small portion of the current is able to concentrate.

Similarly, when a short circuit occurs in a conventional applicator (FIG. 13A), for example, as when a drop of sweat is introduced between the central and annular portions of the applicator, the bulk of the current immediately concentrates and passes through the path of least resistance, i.e., through the short circuit. This is because it is the electrical resistance of the skin which constitutes by far the most important contribution of resistance to current flow in such systems.

By contrast, because in an applicator according to the present invention (FIG. 13B) the resistance offered by the partially conducting layers is a very significant portion of the total resistance, a sudden drop in skin resistance drops the overall resistance to a much lesser degree and therefore, the concentration of current is considerably smaller.

Finally, an applicator according to the present invention (FIGS. 14B and 15B), in contrast with prior art applicators (FIGS. 14A and 15A), can be used to give accurate indications of its improper placement on the skin of the patient.

Shown in FIGS. 14A and 14B is the case where both applicators are properly placed. As described above, the current field produced by an applicator according to the present invention will be much more uniform than that produced by a conventional applicator. However, when the overall potential is measured across either well-placed applicator, the voltage drop will be the same.

Now assume that both applicators are improperly placed so that one portion of each applicator is not in good electrical contact with the skin. In a conventional applicator (FIG. 15A) there will be a concentration of current in those areas where electrical contact is good and the overall voltage drop across the electrodes will be the same as when proper contact is maintained over the entire applicator surface.

By contrast, because the ability of current to concentrate is greatly limited in an applicator according to the present invention (FIG. 15B), the result of improper contact of a portion of the applicator will be a reduced overall voltage drop across the electrodes. Such a voltage drop will give an immediate and accurate indication to the operator of the improper placement of the applicator.

It will be readily appreciated that the scheme represented in the embodiment of FIGS. 11B to 15B can be implemented in geometries other than those involving a central electrode and a surrounding annular electrode. For example, the same scheme can be implemented in the context of the embodiments of FIGS. 1–10 by sizing and dimensioning the electrodes so as to cover only a small fraction of the surface of the partially conduction layer or layers and by placing each of the electrodes near the edge of the applicator which is farthest removed from the other electrode.

It will also be readily appreciated that a scheme such as that described above may be implemented by using electrodes such as those in the embodiments of FIGS. 1–10 which overly all or most of the partially conducting layer or layers, but where other means are used to ensure that different portions of the current see different resistance while traversing the partially conducting layer or layers, for example, by using partially conducting layer or layers having varying thicknesses, and thus resistivities, for different current lines.

While the invention has been described with respect to a limited number of embodiments, it will be appreciated that many variations, modifications and other applications of the invention may be made.

What is claimed is:

1. A transcutaneous iontophoretic chemical applicator for applying a chemical, comprising:
   (a) an array of reservoirs, said reservoirs being electrically insulated from one another, at least one of said reservoirs containing the chemical;
   (b) a partially electrically conducting layer overlying and contacting at least two of said reservoirs, said partially electrically conducting layer being made up of a single layer overlying all of said reservoirs;
   (c) electrodes overlying and physically and electrically contacting said partially electrically conducting layer; and
   (d) an electrical power source electrically connected to said electrodes.

2. An applicator as in claim 1, wherein said electrodes include a single positive electrode and a single negative electrode.

3. An applicator as in claim 1, wherein said electrodes include a plurality of pairs of electrodes, each of said electrodes overlying at least one of said reservoirs.

4. An applicator as in claim 1, wherein said reservoirs contain an electrically conducting material.

5. An applicator as in claim 1, wherein said partially electrically conducting layer is made up of at least two segments, each of said segments overlying some of said reservoirs.

6. An applicator as in claim 2, wherein said partially electrically conducting layer is made up of at least two segments, each of said segments overlying some of said reservoirs.

7. An applicator as in claim 1, wherein said partially electrically conducting layer includes a semiconducting material.

8. An applicator as in claim 7, wherein said partially electrically conducting layer includes silicon and further includes carbon particles.

9. An applicator as in claim 1, wherein said reservoirs are a plurality of regularly shaped volumes integrally formed of electrically insulating material layer.

10. An applicator as in claim 1, wherein said reservoirs are a plurality of microporous volumes integrally formed of electrically insulating material layer.

11. An applicator as in claim 9, wherein said electrically insulating material includes silicon.

12. An applicator as in claim 10, wherein said electrically insulating material includes silicon.

13. An applicator as in claim 1, wherein said electrical power source is a layer power source.

14. An applicator as in claim 1, further comprising a removable seal covering said array of reservoirs which is removed prior to deployment.

15. An applicator as in claim 14 wherein the removal of said removable seal exposes an adhesive.

16. An applicator as in claim 15 wherein said adhesive is located on the exposed surfaces of said array of reservoirs.

17. A transdermal drug applicator for applying a drug, comprising:
   (a) an array of reservoirs, one or more of which contain the drug, said reservoirs being integrally formed in an electrically insulating layer;
   (b) a partially electrically conducting layer located above and in contact with said reservoirs, said partially electrically conducting layer being made up of a single layer overlying all of said reservoirs;
   (c) a pair of electrodes located above and in physical and electrical contact with said partially electrically conducting layer; and
   (d) an electrical power source electrically connected to said pair of electrodes.

* * * * *